US00PP19078P2

(12) United States Plant Patent
Pan

(10) Patent No.: US PP19,078 P2
(45) Date of Patent: Aug. 5, 2008

(54) ***LANTANA* PLANT NAMED 'BANTE ORANSUN'**

(50) Latin Name: *Lantana camara*
Varietal Denomination: Bante Oransun

(75) Inventor: Shifeng Pan, Hollister, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/654,871

(22) Filed: Jan. 17, 2007

(51) Int. Cl.
*A01H 5/00* (2006.01)

(52) U.S. Cl. ..... Plt./227
(58) Field of Classification Search ..... Plt./227
See application file for complete search history.

*Primary Examiner*—Anne Marie Grunberg
*Assistant Examiner*—Louanne C Krawczewicz
(74) *Attorney, Agent, or Firm*—Jondle & Associates, P.C.

(57) ABSTRACT

A *Lantana* plant particularly distinguished by orange flowers, a continuous, abundant and mid-season flowering response, dark green foliage with ovate leaves, vigorous, compact growth, low mounding and good branching ability, is disclosed.

1 Drawing Sheet

Genus and species: *Lantana camara.*
Variety denomination: 'Bante Oransun'.

BACKGROUND OF THE NEW PLANT

The present invention comprises a new and distinct cultivar of *Lantana,* botanically known as *Lantana camara* and hereinafter referred to by the cultivar name 'Bante Oransun'. The new cultivar originated from a pollination made in July 2003 in Gilroy, Calif. The new cultivar was created from the crossing of '22-1', a fuchsia female (unpatented) proprietary line with 'D1-3', a pink male (unpatented) proprietary line.

The new cultivar was created in July of 2003 in Gilroy, Calif. and has been asexually reproduced repeatedly by vegetative cuttings and tissue culture in Gilroy, Calif. and Andijk, The Netherlands over a two and one-half-year period. The plant has also been trialed at Gilroy, Calif., Andijk, The Netherlands and Hillscheid, Germany. The present invention has been found to retain its distinctive characteristics through successive asexual propagations.

Plant Breeder's Rights for this cultivar were applied for in Canada on Mar. 21, 2006 and in Germany on Nov. 27, 2006.

SUMMARY OF THE INVENTION

The following are the most outstanding and distinguishing characteristics of the new cultivar when grown under normal horticultural practices in Gilroy, Calif.

1. Orange flowers;
2. A continuous, abundant and mid-season flowering response;
3. Dark green foliage with ovate leaves;
4. Vigorous growth;
5. A compact and low mounding plant habit; and
6. Good branching ability.

DESCRIPTION OF THE PHOTOGRAPHS

This new *lantana* plant is illustrated by the accompanying photographs which show overall plant habit including blooms, buds and foliage of the plant; the colors shown are as true as can be reasonably obtained by conventional photographic procedures. The photos are of 15-16 week-old plants in September of 2006.

DESCRIPTION OF THE NEW CULTIVAR

Figure 1:
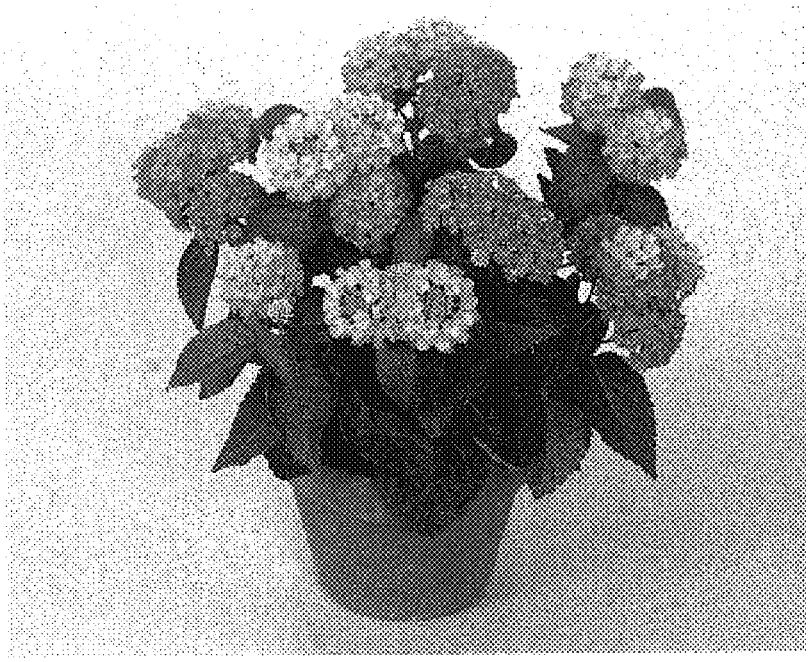
FIG. 1 shows the overall plant habit, including inflorescences, buds and foliage of the whole plant.
Figure 2:
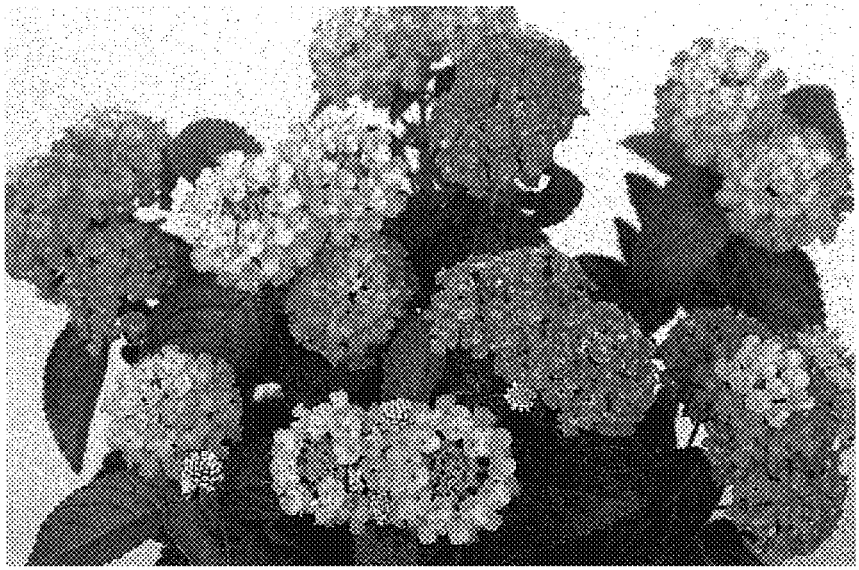
FIG. 2 shows a close-up of several mature inflorescences.

The following detailed descriptions set forth the distinctive characteristics of 'Bante Oransun'. The data which define these characteristics were collected from asexual reproductions carried out in Gilroy, Calif. The plant history was taken on 26-week-old plants, grown in Gilroy, Calif. in 6" pots. Observations were made in summer and early fall. The plants had one plant growth regulator treatment using Sumagic spray at a rate of 10 PPM and one terminal pinch after cuttings were transplanted to the 4" pots then transferred to 6" pots. Color readings were taken under natural light. Color references are primarily to the R.H.S. Colour Chart of The Royal Horticultural Society of London (R.H.S.) (2001 edition).

DETAILED BOTANICAL DESCRIPTION

Classification:
*Family.*—Verbenaceae.
*Botanical.*—*Lantana camara.*
*Common name.*—*Lantana.*
*Denomination.*—'Bante Oransun'.

Parentage:
*Female.*—'22-1', a fuchsia proprietary line (unpatented).
*Male.*—'D1-3', a pink proprietary line (unpatented).

Growth:
*Form.*—Semi-woody, herbaceous; grown as an annual or perennial.
*Growth and branching habit.*—Compact, low mounding, good branching, pinching of the apices enhances the number of branches and results in a tighter plant habit.

*Height* (*measured from the top of the soil*).—12.0 cm to 15.0 cm.

*Width* (*horizontal plant diameter*).—20.0 cm to 23.0 cm.

*Time to produce a finished flowering plant.*—12 to 13 weeks for a 12-cm pot in the spring.

*Outdoor plant performance.*—Use in containers and hanging baskets.

*Time to initiate and develop roots.*—Approximately 24 days.

*Root description.*—Fibrous, fleshy, white, self-branching.

Stems:

*Number of branches per plant.*—7 to 10.

*Length.*—10.0 cm to 12.0 cm.

*Diameter* (*measured from the midpoint*).—0.3 cm.

*Internode length.*—1.5 cm to 2.0 cm.

*Color.*—Immature (growing) stems: RHS 144B. Mature (woody) stems: RHS 152A.

*Anthocyanin.*—Absent.

*Texture.*—Hispid; hirsute; glandular hairs.

Leaves:

*Arrangement.*—Opposite.

*Fragrance.*—Slightly spicy.

*Immature leaf.*—Color: Upper surface: RHS 147A. Lower surface: RHS 137C.

*Mature leaf.*—Color: Upper surface: Closest to RHS 139A, but a little darker. Lower surface: RHS 147A. Length: 6.1 cm to 6.2 cm. Width: 3.4 cm to 4.0 cm.

*Quantity per lateral stem.*—About 8 to 10.

*Shape.*—Ovate to elliptical.

*Apex.*—Acute.

*Base.*—Attenuate.

*Margin.*—Serrate.

*Texture* (*both surfaces*).—Slightly scabrous with some bristles in the mid-vein.

*Venation.*—Pinnate.

*Venation color* (*both surfaces*).—RHS 144A.

*Petioles.*—Length: 1.3 cm to 1.5 cm. Diameter: 0.2 cm. Color: RHS 144A. Texture (both surfaces): Bristles and glandular hairs.

Flower buds:

*Shape.*—Tubular.

*Length.*—0.8 cm to 1.0 cm.

*Diameter* (*at the tip*).—0.3 cm to 0.4 cm.

*Color* (*at tight bud*).—RHS 15A.

Inflorescence:

*Blooming habit.*—Flowers continuously from Spring through Fall; Inflorescences usually appear in pairs with one inflorescence per leaf axil.

*Fragrance.*—Slightly spicy.

*Inflorescence type.*—Umbel-like flattened semi-sphere, subtended by a ring of leaflets, florets are flowers that are sessile on an ovate receptacle.

*Lastingness of inflorescences on the plant.*—About one month.

*Horizontal diameter of inflorescence.*—3.0 cm to 3.75 cm.

*Vertical depth of inflorescence.*—1.5 cm to 2.0 cm.

*Number of inflorescences per plant.*—21 to 29.

*Number of florets per inflorescence.*—25 to 30.

*Peduncle.*—Length: 1.0 cm to 1.2 cm. Diameter: 0.1 cm. Color: RHS 144B. Texture: Hispid; hirsute; glandular hairs.

*Pedicels.*—None, flowers are sessile.

Flowers:

*Floret form.*—Salver-shaped to shallow cup-shaped and zygomorphic, with a relatively long tube at the base. Each flower is subtended by a single bract.

*Corolla diameter.*—0.8 cm to 0.9 cm.

*Floret depth.*—1.5 cm to 1.7 cm.

*General color.*—Mostly yellow-goldish in the very opening stages, then turning through varying hues of medium orange, with deeper orange mature florets. Color intensities can vary with cultural growing conditions.

*Immature flower* (*face*).—Color: Upper surface: RHS 14A; changing to having RHS N25C at the margins. Lower surface: RHS 13B to RHS 13C.

*Mature flower* (*face*).—Color: Upper surface: RHS N25A, some with RHS N25C at the margins then maturing to between RHS N30B to RHS N30D. Lower surface: RHS 26C. Corolla tube: Color: Inner surface: RHS 26D. Outer surface: RHS 26C. Texture (both surfaces): Densely pubescent, some with RHS 33B red-orange hues. Length: 1.0 cm to 1.2 cm. Diameter (at opening): 0.15 cm.

*Petals.*—Number of petals per flower and arrangement: Composed of five petals that are mostly fused; salver-shaped (salverform) to shallow-cup shaped and zygomorphic with a relatively long tube at the base. Number of lobes per petal: Two. Length of lobe: 0.4 cm to 0.5 cm. Diameter of lobe: 0.3 cm to 0.4 cm. Lobe shape: Obovate. Apex: Slightly emarginate. Base: Fused. Margin: Entire. Degree of lobation: Moderate. Texture (both surfaces): Papillose.

*Bract.*—Color: RHS 144B with RHS 144A at the apex. Length: 0.5 cm to 0.6 cm. Diameter: 0.2 cm. Shape: Short, lanceolate. Apex: Acute. Margin: Entire. Base: Fused. Texture: Densely pubescent; hispid.

*Calyx.*—General: Composed of 5 fused sepals forming a short tube around the base of each floret. Shape: Tube-shaped with two short lobes. Length: 0.15 cm to 0.2 cm. Diameter: 0.1 cm. Color (both surfaces): RHS 144C. Apex (of calyx lobe): Rounded. Base (of sepals): Fused. Margin (of sepals): Side-margins are fused, but tips are shallowly fringed. Texture: Densely pubescent.

Reproductive organs:

*Stamens.*—Quantity: 4. Filament color: RHS 2D. Filament diameter: 0.05 cm. Filament length: 0.6 cm to 0.8 cm. Anther color: RHS 17D. Anther length: 0.75 cm. Anther shape: Ovate. Pollen amount: Sparse to none. Pollen color: RHS 16C.

*Pistil.*—Quantity: One. Length: 0.3 cm. Stigma color: RHS 151C. Style color: RHS 1C with slight brown striations. Style length: 0.25 cm.

Fruit/seed set: No fruit or seed has been produced.

Disease and insect resistance: Resistance and susceptibility is typical of the species.

COMPARISON WITH PARENTAL AND COMMERCIAL CULTIVARS

'Bante Oransun' differs from the female parent '22-1' in that 'Bante Oransun' has an orange flower color while the female parent has a fuchsia flower color. In addition, 'Bante Oransun' flowers about 6 days earlier and is more floriferous than the female parent.

'Bante Oransun' differs from the male parent 'D1-3' in that 'Bante Oransun' has an orange flower color, while the male parent has a pink flower color. In addition, 'Bante Oransun' is more compact, has better branching and flowers earlier than the male parent.

'Bante Oransun' differs from the commercial variety 'Balucpea' (U.S. Plant Pat. No. 16,520) in that 'Bante Oransun' has a more compact plant habit with better basal branching. In addition, 'Bante Oransun' has a more golden 'peach' flower color than 'Balucpea'.

I claim:

1. A new and distinct cultivar of *Lantana* plant as shown and described herein.

* * * * *